United States Patent [19]
Grollier et al.

[11] Patent Number: 4,808,190
[45] Date of Patent: * Feb. 28, 1989

[54] PROCESS FOR DYEING KERATINOUS FIBERS WITH 5,6-DIHYDROXY-INDOLE AND HYDROGEN PEROXIDE, PRECEDED OR FOLLOWED BY A TREATMENT WITH AN IODIDE

[75] Inventors: Jean F. Grollier, Paris; Didier Garoche, Levallois-Perret, both of France

[73] Assignee: L'Oreal, Paris, France

[ * ] Notice: The portion of the term of this patent subsequent to Feb. 14, 2006 has been disclaimed.

[21] Appl. No.: 4,497

[22] Filed: Jan. 20, 1987

[30] Foreign Application Priority Data

Jan. 20, 1986 [LU] Luxembourg .................. 86256

[51] Int. Cl.$^4$ ................................................. A61K 7/13
[52] U.S. Cl. ........................................ 8/423; 8/406; 8/634
[58] Field of Search ................ 8/404, 405, 406, 423, 8/634

[56] References Cited

U.S. PATENT DOCUMENTS

| 1,677,508 | 7/1928 | Winogradoff et al. | 8/405 |
| 2,934,396 | 4/1960 | Charle et al. | 8/593 |
| 4,208,183 | 6/1980 | Grollier et al. | 8/609 |

FOREIGN PATENT DOCUMENTS

| 1469739 | 1/1969 | Fed. Rep. of Germany . |
| 2028818 | 12/1970 | Fed. Rep. of Germany . |
| 1116172 | 6/1958 | France . |
| 1264707 | 5/1961 | France . |
| 1365276 | 5/1964 | France . |
| 2486395 | 1/1982 | France . |
| 1133594 | 11/1986 | France . |
| 823503 | 11/1959 | United Kingdom . |
| 2132642 | 7/1984 | United Kingdom . |

*Primary Examiner*—Paul Lieberman
*Assistant Examiner*—Linda D. Skaling
*Attorney, Agent, or Firm*—Cushman, Darby & Cushman

[57] ABSTRACT

The invention relates to a process for dyeing keratinous fibers characterized in that at least one composition comprising, in a medium suitable for dyeing, 5,6-dihydroxyindole in combination with hydrogen peroxide at a pH of between 2 and 7 is applied to these fibers, the application of said composition being preceded or followed by the application of a composition comprising iodide ions in a medium suitable for dyeing.

22 Claims, No Drawings

PROCESS FOR DYEING KERATINOUS FIBERS WITH 5,6-DIHYDROXY-INDOLE AND HYDROGEN PEROXIDE, PRECEDED OR FOLLOWED BY A TREATMENT WITH AN IODIDE

The present invention relates to a new process for colouring keratinous fibres, especially human, with 5,6-dihydroxyindole and to compositions employed in this process.

It is well known that the natural biosynthesis of eumelanins from tyrosine is carried out in several stages. One of them consists in the formation of 5,6-dihydroxyindole which oxidizes to give a pigment which is one of the main constituents of eumelanin.

Many processes for dyeing hair which employ 5,6-dihydroxyindole or some of its derivatives have already been proposed in the past.

Thus, in French Patent No. 1,166,172, a solution of 5,6-dihydroxyindole with an acid pH is applied to the hair for 5 to 60 minutes, and without rinsing and after wringing, the colour is revealed using an oxidizing agent which may especially be hydrogen peroxide.

In French Patent No. 1,133,594, an alkaline solution of 5,6-dihydroxyindole containing, if required, an oxidizing agent or an oxidation catalyst, is applied to the hair. Different oxidizing agents including hydrogen peroxide and oxidation catalysts such as cupric chloride are provided for.

According to this process, it is also possible to operate in two stages, by following the application of 5,6-dihydroxyindole in an alkaline medium by a rinsing and a revealing with an oxidation catalyst.

In French Patent Application No. 2,536,993, a process for dyeing in several stages separated by rinsings and consisting in applying, in a first stage, a metal salt solution with an alkaline pH and, in another stage, a 5,6-dihydroxyindole solution has also been recommended.

These two stages are, after rinsing or shampooing, followed or otherwise by an application of hydrogen peroxide to adjust the final shade by lightening.

These processes of the prior art have different drawbacks insofar as they lead either to shades which are not very strong despite long exposure time, or to the production of strong shades which require a long exposure time and leading to a surface dyeing which is not very fast. The use of some metal salts of groups III to VIII of the periodic classification, the harmlessness of which has not always been demonstrated, may lead, under the conditions of use, to a modification of the cosmetic or mechanical properties of the hair.

Moreover, compositions based on 5,6-dihydroxyindole have problems of stability during storage, especially in an alkaline medium.

The Applicant Company has now discovered, and this forms the subject of the invention, means which enable strong shades to be obtained with 5,6-dihydroxyindole with short exposure times without using any metal or metal salt of groups III to VIII and which employ a solution of 5,6-dihydroxyindole with an acid pH.

Another subject of the invention consists of compositions employed in this process and "kits" or dyeing outfits containing several components which employ these different compounds.

Other subjects of the invention will be apparent on reading the description and the examples which follow.

The process for dyeing keratinous fibres, especially human, according to the invention is essentially characterized in that at least one composition (A) containing, in a medium suitable for dyeing, 5,6-dihydroxyindole in combination with hydrogen peroxide at a pH of between 2 and 7 and preferably between 3.5 and 7 is applied to these fibres, in that the application of this composition (A) is preceded or followed by the application of a composition (B) which contains iodide ions, in a medium suitable for dyeing, the application of compositions (A) and (B) being separated, if required, by a rinsing stage.

The process according to the invention is implemented by preparing the mixture of 5,6-dihydroxyindole and hydrogen peroxide, which forms the composition A, just before use.

The iodide ion is preferably an alkali metal or alkaline-earth metal or ammonium iodide, and more particularly, potassium iodide.

This process is preferably applied to the dyeing of hair, especially living human hair, using, in this case, cosmetically acceptable media.

The fibres may be rinsed between the two stages which enables, among other things, the staining of the scalp to be avoided when the composition is used for dyeing human hair. If, on the hand, no intermediate rinsing is carried out, the exposure time(s) is (are) reduced.

In the compositions employed in the process according to the invention, 5,6-dihydroxyindole is generally present in proportions between 0.01 and 5% by weight, preferably between 0.03 and 3% by weight relative to the total weight of composition A. The proportion of iodide in the compositions of the invention is between 0.007 and 4% by weight expressed as $I^-$ ions and preferably between 0.008 and 2.5% relative to the total weight of composition B.

The 5,6-dihydroxyindole and the iodide ions present in compositions (A) and (B) respectively are preferably employed in such proportions as to have a 5,6-dihydroxyindole/$I^-$ weight ratio of between 0.05 and 10 and especially between 0.5 and 2.

The concentration of hydrogen peroxide in the hydrogen peroxide solutions used is between 1 and 40 volumes, preferably between 2 and 20 volumes, and more particularly between 3 and 15 volumes.

The process is implemented allowing exposure times, for the different compositions applied in each of the different stages of the process, between 10 seconds and 45 minutes and preferably of the order of 2 to 25 minutes and more particularly of the order of 2 to 15 minutes.

The Applicant Company has observed that the process employed enabled colourings to be obtained which are both rapid and strong, which do not risk degrading the fibres and which have a good resistance against washings and to light.

It has also observed that when the process was applied to the dyeing of human hair, the hair dyed several times following regrowth was softer, shinier, and had good mechanical properties compared with hair dyed using processes and compositions of the prior art.

Relatively intense colourings are obtained in fairly short times, of the order of 5 to 15 minutes.

The compositions used for implementing the process according to the invention maybe present in diverse forms, commonly used for dyeing such as more or less thickened or gellified liquids, creams, emulsions, foams or other forms suitable for carrying out dyeing.

The compositions employed in the process according to the invention, containing either 5,6-dihydroxyindole or iodide ions, generally comprise a cosmetic medium either aqueous consisting of water or a water-solvent(s) mixture, or based on anhydrous solvent(s), the solvent(s) being one or more organic solvent(s) preferably chosen from ethyl alcohol, propyl or isopropyl alcohol, tert-butyl alcohol, ethylene glycol, monomethyl, monoethyl and monobutyl ethers of ethylene glycol, ethylene glycol monoethyl ether acetate, propylene glycol, monomethyl ethers of propylene glycol and dipropylene glycol and methyl lactate.

A solvent containing less than 1% of water is called an anhydrous solvent.

Preferred solvents are ethyl alcohol and propylene glycol.

When the medium consists of a water-solvent mixture, the solvents are present in concentrations preferably between 0.5 and 75% and especially between 2 and 50% by weight relative to the total weight of the composition.

When the medium is aqueous, the pH of the composition containing iodide ions is between 2 and 11 and preferably between 2 and 7.

The compositions used in accordance with the process according to the invention may also contain fatty amides such as mono- and diethanolamides of acids derived from coconut, lauric acid, oleic acid, at concentrations between 0.05 and 10% by weight.

These compositions may also contain anionic, cationic, nonionic, or amphoteric surfactants or their mixtures. These surfactants are preferably used in proportions between 0.1 and 50% by weight relative to the total weight of the composition and advantageously between 1 and 20% by weight.

The compositions defined above may be thickened with thickening agents such as sodium alginate, gum arabic, guar gum, biopolymers such as xanthan gum or scleroglucans, cellulose derivatives such as methyl cellulose, hydroxyethyl cellulose, hydroxypropylmethyl cellulose, sodium salt of carboxymethyl cellulose and acrylic acid polymers. Inorganic thickening agents such as bentonite may also be used. These thickeners are used alone or in mixture and are preferably present in proportions between 0.1 and 5% by weight relative to the total weight of the composition and advantageously between 0.5 and 3%.

The alkalinizing agents which can be used in these compositions may be especially amines such as alkanolamines, alkylamines, alkali metal or ammonium hydroxides or carbonates. The acidifying agents which can be used in the compositions according to the invention may be chosen from lactic acid, acetic acid, tartaric acid, phosphoric acid, hydrochloric acid and citric acid. It is possible to use any other alkalinizing or acidifying agent.

It is possible to add, if required, to each of the compositions a swelling agent for the keratinous fibre such as, for example, urea.

The compositions employed in the process according to the invention may additionally contain different adjuvants such as perfumes, sequestrants, film-forming products, treatment agents, dispersants, hair conditioning agents, preservatives and opaqueing agents.

When the composition containing 5,6-dihydroxyindole or iodide ions is used in the form of a foam, it may be packaged under pressure in an aerosol device in the presence of a propellant and at least one foam generator. Foam generating agents may be anionic, cationic, nonionic or amphoteric foaming polymers or the surfactants defined above.

With a view to implementing the process according to the invention, the compositions may be packaged in devices with several compartments, also called "kits" or dyeing outfits containing all the components intended to be applied for a same dyeing to keratinous fibres in successive applications, with pre-mixing. Such devices in themselves are known.

According to one embodiment, the "kit" or the dyeing outfit comprises a first compartment containing a composition which contains iodide ions in a medium suitable for dyeing, a second compartment containing a composition which contains 5,6-dihydroxyindole in a medium suitable for dyeing and a third compartment containing a composition of 1 to 40 volume hydrogen peroxide at a pH of between 2 and 7 and preferably between 2 and 5, the composition contained in the third compartment being intended to be mixed with the contents of the second compartment at the time of use.

In this embodiment, it is possible to store the iodide ions and/or the 5,6-dihydroxyindole in an anhydrous solvent medium and to carry out their mixing with an aqueous medium suitable for dyeings at the time of use. This medium may be contained in a fourth compartment of the device.

When the medium suitable for dyeing is aqueous, the pH of the composition of the first compartment is between 2 and 11 and that of the composition of the second compartment is between 2 and 7 and preferably between 3.5 and 7.

The devices may be quipped with means for mixing at the time of use, which are known in themselves and may be packaged in an inert atmosphere.

The process according to the invention and the compositions employed may be used for dyeing natural or already dyed hair, permed or otherwise, or uncurled, or strongly or lightly bleached and possibly permed hair.

The compositions may also be used for the dyeing of furs or wool.

The following examples are intended to illustrate the invention without thereby implying a limiting nature.

EXAMPLE 1

A colouring of permed white hair is carried out by applying successively two compositions packaged in a dyeing "kit" with three compartments, the application of the compositions being separated by a rinsing with water.

Composition B

Potassium iodide: 1.5 g
Urea: 4.5 g
Lactic acid qs ph: 5
Water qs 100 g.

Composition A 7.5 volume $H_2O_2$: 50 g
N,N-Dimethylethanolamine qs pH: 6.5
5,6-Dihydroxyindole: 1 g
Ethyl alcohol: 10 g
Water qs 100 g.

Composition B is packaged in the first compartment of the "kit". Composition A is prepared at the time of use by mixing the contents of the other two compartments of the "kit", containing respectively:
In one:
aqueous solution of 7.5 volume $H_2O_2$: 50 g pH =6.5.
In the other:
5,6-dihydroxyindole: 1 g
ethyl alcohol: 10 g
N,N-dimethylethanolamine qs pH: 6.5
water qs 50 g.
The hair is exposed to composition B for 5 minutes, rinsed and composition A is then applied for 5 minutes. A black colour is obtained.

EXAMPLE 2

A colouring of natural white hair is carried out by successively applying two compositions packaged in a dyeing "kit" with three compartments.

Composition 1

5,6-dihydroxyindole: 1 g
Propylene glycol: 5 g
Water qs 50 g
Spontaneous pH: 6.

This composition 1 packaged in one of the compartments of the kit is mixed at the time of use with 50 g of an aqueous solution of 12.5 volume $H_2O_2$ with a pH of 4, contained in a second compartment of the kit to obtain composition A.

This composition is applied to the hair. The hair is exposed for 5 minutes. It is rinsed with water.

A composition B packaged in the 3rd compartment of the kit is then applied to the hair.

Composition B

Potassium iodide: 1.5 g
Water qs 100 g
Spontaneous pH: 6.

The hair is exposed for 10 minutes. After rinsing with water and drying, a medium grey colour is obtained.

EXAMPLE 3

Example 2 is repeated, without carrying out an intermediate rinsing between the application of the two compositions A and B. A black colour is obtained.

EXAMPLE 4

A colouring of 90% white hair is carried out by applying successively two compositions packaged in a dyeing "kit" with 3 compartments.

Composition A 5,6-dihydroxyindole: 0.1 g
Ethyl alcohol: 4 g
10 volume $H_2O_2$: 50 g
Water qs 100 g
pH: 3.8.

Composition B

Potassium iodide: 0.13 g
Guar gum sold under the name Jaguar HP 60 by Celanese: 1 g
Glycoside alkyl ether sold at a 60% AS under the name Triton CG 110 by Seppic: 5 g AS
Water qs 100 g
Citric acid qs : pH : 3.

Composition B is packaged in the first compartment of the "kit".

Composition A is prepared at the time of use by mixing the contents of the other two compartments of the "kit", containing respectively:
In one:
Aqueous composition of 10 volume $H_2O_2$ with a pH of 3.5: 50 g
In the other:
5,6-dihydroxyindole: 0.1 g
Ethyl alcohol: 4 g
Water qs 50 g
pH: 5.8.
The hair is exposed to Composition B for 15 minutes and, without rinsing Composition A is then applied for 2 minutes.

After rinsing with water and drying, a light grey colour is obtained.

EXAMPLE 5

A colouring of 90% white hair is carried out by applying successively two compositions A and B packaged in a dyeing "kit" with 3 compartments, the application of the compositions being separated by a rinsing with water.

Composition A 5,6-dihydroxyindole: 5 g
Ethylene glycol monoethyl ether: 15 g
40 volume $H_2O_2$: 50 g
Water qs 100 g
pH: 6.3.

Composition B

Sodium iodide: 4.7 g
Water qs 100 g
Triethanolamine qs pH : 8

Composition B is packaged in the first compartment of the "kit".

Composition A is prepared at the time of use by mixing the contents of the other two compartments of the "kit", containing respectively:
In one:
Aqueous composition of 40 volume $H_2O_2$ with a pH of 6: 50 g
In the other:
5,6-dihydroxyindole: 5 g
Ethylene glycol monoethyl ether 15 g
Water qs 50 g
pH: 6.2

The hair is exposed to Composition A for 4 minutes, rinsed with water and Composition B is then applied and the hair is exposed for 15 minutes.

After rinsing with water and drying, a medium grey colour is obtained.

EXAMPLE 6

A colouring of 90% white hair is carried out by applying successively two compositions A and B packaged in a dyeing "kit" with 3 compartments:

Composition A 5,6-dihydroxyindole: 0.2 g
Ethyl alcohol: 5 g
Guar gum sold under the name Jaguar HP 60 by Celanese: 1 g
Glycoside alkyl ether sold at a 60% AS concentration under the name Triton CG 110 by Seppic: 5 g AS
10 volume H$_2$O$_2$: 50 g
Water qs 100 g
pH: 5.9.

Composition B

Potassium iodide: 0.26 g
Water: 100 g
N,N-dimethylethanolamine qs pH : 11

Composition B is packaged in the first compartment of the "kit"

Composition A is prepared at the time of use by mixing the contents of the other two compartments of the "kit", containing respectively:

In one:
Aqueous composition of 10 volume H$_2$O$_2$ with a pH of 3: 50 g

In the other:
50 g of the following composition:
5,6-Dihydroxyindole: 0.4 g
Ethyl alcohol: 5 g
Guar gum sold under the name Jaguar HP 60 by Celanese: 1 g
Glycoside alkyl ether sold at a 60% AS concentration under the name Triton CG 110 by
Seppic: 5 g AS
Water qs 100 g
pH: 6.6.

The hair is exposed to Composition A for 15 minutes and Composition B is then applied, without rinsing, and the hair is exposed for 3 minutes.

After rinsing with water and drying, a light grey colour is obtained.

We claim:

1. Process for dyeing keratinous fibers, characterized in that at least one composition (A) comprising, in a medium suitable for dyeing, 5,6-dihydroxyindole in proportions of between 0.01 and 5% by weight in combination with hydrogen peroxide at a concentration from 1 to 40 volumes at a pH of between 2 and 7 is applied to these fibers, the application of composition (A) being preceded or followed by the application of composition (B) comprising iodide ions in proportions of between 0.007 and 4% by weight expressed as I$^-$ ions in a medium suitable for dyeing.

2. Process according to claim 1, wherein composition B comprises iodides chosen from the group consisting of alkali metal, alkaline-earth metal and ammonium iodides.

3. Process according to claim 1, wherein the application of compositions (A) and (B) of the process is separated by a rinsing stage.

4. Process according to claim 1, wherein the process is implemented without rinsing between the application of compositions (A) and (B).

5. Process according to claim 1, characterized in that the 5,6-dihydroxyindole is present in composition A in proportions of between 0.03 and 3% by weight.

6. Process according to claim 1, wherein the proportion of iodide ions in composition B is between 0.008 and 2.5% by weight expressed as I$^-$ ions.

7. Process according to claim 1, wherein the 5,6-dihydroxyindole and the iodide ions present in compositions (A) and (B) respectively are employed in such proportions as to have a 5,6-dihydroxyindole/I$^-$ ratio of between 0.05 and 10.

8. Process according to claim 1, wherein aqueous solutions of hydrogen peroxide at a concentration from 2 to 20 volumes, are used in composition (A).

9. Process according to claim 1, wherein compositions (A) and (B) are applied with exposure times between 10 seconds and 45 minutes.

10. Process according to claim 1, wherein the composition B containing the iodide ions comprises an anhydrous solvent medium consisting of at least one anhydrous solvent.

11. Process according to claim 1, wherein the composition B containing the iodide ions is aqueous and in that it has a pH of between 2 and 11.

12. Process according to claim 10, wherein the anhydrous solvent is selected from the group consisting of ethyl alcohol; propyl alcohol; isopropyl alcohol; tertbutyl alcohol; ethylene glycol; monomethyl, monoethyl and monobutyl ethers of ethylene glycol;; ethylene glycol monoethyl ether acetate; propylene glycol; monomethyl ethers of propylene glycol and dipropylene glycol; methyl lactate; and mixtures thereof.

13. Process according to claim 1 wherein at least one of compositions (A) and (B) further comprise at least one adjuvant selected from the group consisting of
a fatty amide present in an amount ranging from 0.05 to 10 weight percent,
a surfactant selected from the group consisting of an anionic, cationic, nonionic, amphoteric surfactant and mixtures thereof present in an amount ranging from 0.1 to 50 weight percent,
a thickening agent selected from the group consisting of sodium alginate, gum arabic, guar gum, xanthan gum, scleroglucan, cellulose derivative, acrylic acid polymer, bentonite and mixtures thereof present in an amount ranging from 0.1 to 5 weight percent,
an alkalizing agent,
an acidifying agent,
a perfume,
a sequestrant,
a film-forming agent,
a dispersant,
a conditioning agent,
a preservative,
an opaqueing agent and
a swelling agent for fibers.

14. Process according to claim 1 wherein the keratinous fibers are human hair.

15. Process according to claim 1, wherein the pH of composition (A) is between 3.5 and 7.

16. Process according to claim 7, wherein the ratio of dihydroxyindole/I$^-$ is between 0.5 and 2.

17. Process according to claim 11, wherein the pH of composition (B) is between 2 and 7.

18. Process according to claim 11, wherein composition (B) comprises water and at least one other solvent selected from the group consisting of ethyl alcohol; propyl alcohol; isopropyl alcohol; tert-butyl alcohol; ethylene glycol; monomethyl, monoethyl and monobutyl ethers of ethylene glycol; ethylene glycol monoethyl ether acetate; propylene glycol; monomethyl ethers of propylene glycol and dipropylene glycol; methyl lactate; and mixtures thereof.

19. Device with several compartments or "kit" for dyeing keratinous fibers, comprising a first compartment containing a composition comprising iodide ions in proportions of between 0.007 and 4% by weight as I$^-$ ions in a medium suitable for dyeing, a second compartment containing a composition comprising 5,6-dihydroxyindole in proportions of between 0.01 and 5% by weight in a medium suitable for dyeing, and a third compartment containing a composition of 1 to 40 volume hydrogen peroxide at a pH of between 2 and 7, the composition contained in the third compartment being intended to be mixed with the contents of the second compartment at the time of use.

20. Device according to claim 19, wherein the media suitable for dyeing present in the first and second compartments are aqueous and have, in the case of the medium contained in the first compartment, a pH of between 2 and 11, in the case of the medium contained in the second compartment, a pH of between 2 and 7.

21. Device according to claim 19, wherein the iodide ion or the 5,6-dihydroxyindole or both the iodide ion and the 5,6-dihydroxyindole are in an anhydrous solvent medium.

22. Device according to claim 21 further comprising a fourth compartment containing an aqueous medium suitable for dyeing intended to be mixed with the contents of the first or the second compartment or both the first and second compartments at the time of use.

* * * * *